United States Patent
Kim et al.

(10) Patent No.: US 6,193,896 B1
(45) Date of Patent: Feb. 27, 2001

(54) METHOD FOR REMOVAL OF LEUCOCYTES FROM BLOOD

(75) Inventors: Jae-Jin Kim; Sang-Bong Suh; Byung-Ok Jung, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 09/507,082

(22) Filed: Feb. 18, 2000

Related U.S. Application Data

(62) Division of application No. 09/040,389, filed on Mar. 18, 1998.

(30) Foreign Application Priority Data

Jun. 4, 1997 (KR) .................................. 97-23052

(51) Int. Cl.$^7$ .................................. B01D 37/00
(52) U.S. Cl. .................... 210/767; 210/504; 210/506; 210/507; 210/490; 436/177
(58) Field of Search .................... 210/490, 503, 210/505, 506, 507, 508, 645, 767, 504; 424/402, 443, 486, 488; 427/512, 513, 600, 601; 435/2; 436/177, 178

(56) References Cited

U.S. PATENT DOCUMENTS

| | | | |
|---|---|---|---|
| 4,701,267 | 10/1987 | Watanabe et al. | 210/806 |
| 4,880,548 | 11/1989 | Pall et al. | 210/767 |
| 4,923,620 | 5/1990 | Pall et al. | 210/767 |
| 5,114,788 | 5/1992 | Nakagawa et al. | 428/284 |
| 5,259,950 | 11/1993 | Shiro et al. | 210/490 |
| 5,320,903 | 6/1994 | Hirukawa et al. | 428/364 |
| 5,378,472 | 1/1995 | Muzzarelli | 424/445 |
| 5,407,581 | 4/1995 | Onodera et al. | 210/654 |
| 5,420,197 | 5/1995 | Lorenz et al. | 525/543 |
| 5,618,622 | 4/1997 | Gillberg-Laforce et al. | 428/357 |
| 5,759,570 | 6/1998 | Arnold | 424/443 |

FOREIGN PATENT DOCUMENTS 0 397 403    11/1990    (EP) .

OTHER PUBLICATIONS

Bruil, et al., "Poly(ethyleneimine) modified filters for the removal of leukocytes from blood," *J. of Biomed. Mat. Res.*, vol. 27, pp. 1253–1268 (1993).

Nishimura, et al., "Advanced methods for leucocyte removal by blood infiltration," B. Brozovic ed., *Blackwell Scientific Publications*, Oxford, pp. 35–40 (1989).

Seyfert, et al., Adhesion of leucocytes to microscope slides as influenced by electrostatic interaction, *Biomaterials*, vol. 16, No. 3, pp. 201–207 (1995).

*Primary Examiner*—John Kim
(74) *Attorney, Agent, or Firm*—Oblong, Spivak, McClelland, Maier & Neustadt, P.C.

(57) ABSTRACT

Filter for removal of leucocytes is provided, wherein the filter is coated with a natural polymer of chitosan which has a good blood compatibility and no side effect in human body on an ultrafine non-woven fabric. This blood filter provides a high removal rate of leucocytes as well as good recovery of platelets and red blood cells due to secondary filtration through electrostatic power between a leucocyte and a cationic residue provided by chitosan on the surface of the non-woven fabric.

2 Claims, No Drawings

METHOD FOR REMOVAL OF LEUCOCYTES FROM BLOOD

This application is a Division of application Ser. No. 09/040,389 Filed on Mar. 18, 1998.

BACKGROUND OF THE INVENTION

1. Field of the Invention

The present invention relates to a filter for removal of leucocytes coated with a natural polymer of chitosan. More particularly, the invention relates to a filter for removal of leucocytes prepared by applying a natural polymer of chitosan on ultrafine non-woven fabric, wherein said polymer has a good blood compatibility while avoiding negative side-effects in a human body. The filter for removal of leucocytes of the invention has a high removal rate of leucocytes with good recovery of platelets and red blood cells.

2. Description of the Prior Art

Blood occupies about 6 to 8%by weight of human body, and about 40 to 45% by volume of blood is solid phase and the rest is liquid phase. The solid cell components of blood consist of red blood cells (RBC), leucocytes and platelets, and the liquid components of blood, so-called plasma, consist of a solution of plasma protein such as fibrinogen, albumin and gamma-globulin, and organic and inorganic salts in water. As disclosed above, blood is important and valuable as a structural component of the human body as well as functional component. Recently, a trend in blood transfusion has been changing from transfusing a whole blood to a active transfusion of only desired blood components, and such transfusion is commonly utilized in blood transfusion therapy. The blood components transfusion therapy has an advantage in that it is possible that sufficient amounts of particular blood components are provided to a patient in need of such components. Additionally, it is possible to use a single unit of donated blood in larger patients, thereby avoiding waste of blood resources.

After transfusion of a blood preparation of red cell or platelet concentrates as well as a fresh whole blood, leucocytes contained in the preparation may result in several side effects such as non-hemolytic pyrexia and transfusion refractoriness due to forming of anti-leucocyte antibodies. In particular, repeated transfusions of platelet concentrates frequently leads to alloimmunization against histocompatible antigen of leucocytes contained therein. Thus, in order to reduce such leucocyte-associated post-transfusion complications, it is desirable to remove leucocytes from platelet concentrates.

Amongst the various techniques to remove leucocytes from blood, platelet separation aphersis has been recommended since it can reduce the number of donors. Also, conventional methods such as centrifugal settlements and washing with physiological saline may be utilized in the removal of leucocytes. Recently, a filtration through a filter has been developed and is beginning to replace centrifugation and washing processes. Since the filtration is conducted by using a disposable filter, inflammation can be avoided. Also, by using gravity, separate additional devices are unnecessary. This filtration process has advantages in that removal efficiency of leucocytes is high, and the time required is short.

Seyfert et al. disclosed that cell adhesion was increased by coating a microscope slide matrix with polycations. They reported that cell adhesion rate on the matrices was influenced more by electrostatic interaction due to surface charge rather than by surface tension (See, S. Seyfert, A. Voigt and D. Kabbeck-Kupijai, "Adhesion of Leucocyte to Microscope Slides as Influenced by Electrostatic Interaction", *Biomaterials*, Vol. 16, No. 3, pp 210–207, (1995)).

Nishimura et al. disclosed that when non-woven fabric of polyester is used to remove leucocytes, as the fibre diameter of the fabric is made smaller, the removal rate of leucocytes becomes higher. Also, they reported that non-woven fabric having its surface coated with a random copolymer of hydroxyethylmethacrylate and diethylaminoethylmethacrylate has cationic potential [See, T. Nishimura, T. Kuroda, Y. Mizoguchi, H. Watanabe, H. Rikumaru and M. Umegae, "Advanced Method for Leucocyte Removal by Blood Filtration" in "The Role of Leucocyte Depletion in Blood Transfusion Practice", B. Brozovic ed., Blackwell Scientific Publications, Oxford (1989) pp 35–40].

Further, Bruil et al. carried out an experiment in which non-woven fabrics of polyurethane coated with poly (ethyleneimine) were used as a filter in order to investigate its effect on the leucocytes adhesion during filtration, and they confirmed that leucocytes adhered to the surface of the filter through selective interaction with its amine group [See, A. Bruil, H. A. Oosterom, I. Steneker, B. J. M. Al, T. Beugeling, W. G. van Aken, and J. Feijin, "Poly (ethyleneimine) Modified Filters for the Removal of Leucocytes from Blood", *J. Biomed. Mat. Res.*, Vol. 27, pp 1253–1268 (1993)].

Recently, filters for removal of leucocytes have been clinically utilized, and devices and methods for blood filtration using a fiber filter having surface modified with various polymers are disclosed in the many patent publications (See, U.S. Pat. No. 4,923,620, U.S. Pat. No. 4,880,548, U.S. Pat. No. 4,701,267, EP 0 397 403 A1, EP 0 408 462 A2 and EP 0 406 485 A1). However, no patent publication teaches that a non-woven fabric having its surface coated with chitosan may be used as a blood filter.

According to the present invention, excellent effects can be accomplished by using a natural biocompatible polymer, not using a synthetic polymer as a coating solution for non-woven fabric.

The present inventors have carried out many investigations in order to increase the biocompatibility of the filter for blood filtration. As a result, it has been found that a filter having improved properties can be obtained by newly applying chitosan as a coating material on non-woven fabric which have been used as a conventional filter material. In accordance with the present invention, there is provided a filter for removal of leucocytes having a sufficient removal efficiency of leucocytes and recovery of red blood cells or platelets without causing any side effects in the human body. The above result is consistent with a removal rate of leucocytes of at least 95% and a recovery of red blood cells of at least 90% and a recovery of platelets of at least 90% as recommended by the American Association of Blood Banks.

SUMMARY OF THE INVENTION

It is an object of the invention to provide a filter for removal of leucocytes comprising non-woven fabric having its surface coated with chitosan.

In accordance with the present invention, it is preferably provided a filter for removal of leucocytes comprising a natural or synthetic non-woven fabric having not more than 3 μm of pore size which is coated with chitosan having a deacetylation degree of 85 to 95% and an average molecular weight of 200,000 to 700,000.

It is further object of the invention to provide a method for preparing the filter for removal of leucocytes comprising the step of applying a solution of chitosan onto non-woven fabric.

In accordance with the present invention, the filter for removal of leucocytes is preferably prepared by immersing non-woven fabric in a solution of 0.1 to 5% chitosan in organic or inorganic acid for 30 to 120 minutes, and optionally, subjecting the solution to ultrasonic treatments for not more than 2 hours during the immersing procedure.

DETAILED DESCRIPTION OF THE INVENTION

In accordance with the present invention, the principle of removing leucocytes is based on the following:

Firstly, leucocytes of 6–20 μm in size are removed through non-woven fabric of ultrafine fibers, and platelets of 2–4 μm and red blood cells of 6–9 μm in size pass through the fabric. The secondary mechanism of filtration is effected by the electrostatic power between a leucocyte and a cationic residue on the surface of the coated non-woven fabric. In comparison, an experiment carried out with a conventional filter comprising only non-woven fabric showed that the recovery of red blood cells and platelets depends on the pore size of the non-woven fabric, whereas the removal rate of leucocytes depends more on surface adhesion.

Blood cells are mixture of lipid and protein that is a complex of amino acid, and are anionic. Accordingly, the filter for removal of leucocytes of the invention uses chitosan as an adhesive base having cationic potential to which blood cells can adhere by electrostatic interaction.

Generally, chitosan is a deacetylated form of chitin, a kind of carbohydrate derivatives derived from fungi, yeast, shrimp, crab and other oceanic invertebrates. The chemical name of chitosan is (1→4)2-amino-2-deoxy-β-D-glucosamine having the chemical structure, as shown in the general formula (1):

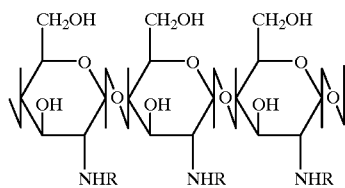

(1)

As known from the above formula, chitosan has a cationic functional group to which a leucocyte is able to adhere to because of an anionic charge on its surface. Also, chitosan is harmless and innoxious to human body. Therefore, it may be efficiently utilized in the filter for removal of leucocytes by modifying surface of the filter with it. In the present invention, it is more preferable to use chitosan having a deacetylation degree of 85–95% and an average molecular weight of 200,000–700,000.

According to the invention, non-woven fabric to provide the primary filtration mechanism by pore size between adjacent fibers may be several natural or synthetic non-woven fabrics including polyester, polyamide, cellulose and other cellulose derivatives. It is preferable to use a non-woven fabric having not more than 3 μm of pore size, about 1.8 μm of fiber diameter and about 0.15 g/cm³ of bulk density. More preferably, ultrafine non-woven fabric of polyester having the above characteristics is used.

The filter for removal of leucocytes of the invention can be prepared by immersing a non-woven fabric in said solution of chitosan, or spraying the above solution onto the non-woven fabric. For example, when coating method of immersing in the solution of chitosan was used, it is preferable to immerse the non-woven fabric in a solution of 0.1–5% by weight of chitosan in organic acid, such as acetic acid and formic acid, and inorganic acid for 30–120 minutes. More preferably, it can be further treated by ultrasonic treatment of the solutions for not more than 2 hours during the immersing procedure.

The filter of the invention can be utilized in the filtration of a whole blood and in the preparation of several blood components according the conventional methods of the prior art.

DESCRIPTION OF THE PREFERRED EMBODIMENTS

The present invention will be illustrated in greater detail by way of the following examples. The examples are presented for illustrative purposes only and should not be construed as limiting the invention. In the examples, the removal rate of leucocytes and the recovery of platelets and red blood cells were calculated from values obtained by using a blood cell analyzer according to the following arithmetic equation.

Removal rate (%) of leucocytes=[1−number of leucocytes after filtration/number of leucocytes before filtration]×100

Recovery (%) of platelets=[number of platelets after filtration/number of platelets before filtration]×100

Recovery (%) of red blood cells=[number of red blood cells after filtration/number of red blood cells before filtration]×100

EXAMPLE 1

Chitosan having an average molecular weight of 500,000 and a deacetylation degree of 92% obtained from shrimp was dissolved in 1% acetic acid to obtain a solution of 0.5% chitosan of 500 ml. A medical ultrafine polyester non-woven fabric (30 mm×30 mm×1.8 mm, Lydall Co., U.S.A.) having a pore size of 3 μm, a fiber diameter of 1.8 μm and bulk density of 0.156 g/cm³ was immersed into the solution at 25° C. for 60 minutes. Then, the non-woven fabric was removed from the solution, and dried at 40° C. for about 50 minutes and then dried in a drying oven at 20–25° C. for about 24 hours. This non-woven fabric was used as a filter for removal of leucocytes.

Through a filtration kit comprising the filter, two 600 ml units of a whole blood preparation, obtained from the Red Cross Blood Banks, were filtered at room temperature with the rate of about 13 to 15 minutes per unit. A blood cell analyzer (Cell-dyn 900, SeQuoia-Turner Co., U.S.A.) was used to determine the number of blood cells before and after filtration. The removal rate of leucocytes and the recovery of platelets and red blood cells were found to be 99%, 95% and 95%, respectively.

EXAMPLE 2

The procedures as described in Example 1 were repeated to prepare a filter except that a solution of 3% chitosan in 1% acetic acid was used as a coating solution. The removal rate of leucocytes and the recovery of platelets and red blood cells were calculated after filtration of whole blood under the same condition as described in Example 1, and the results were 96%, 95% and 95%, respectively.

EXAMPLE 3

The procedures as described in Example 1 were repeated to prepare a filter except that a solution of 5% chitosan in 1% acetic acid was used as a coating solution. The removal rate of leucocytes and the recovery of platelets and red blood cells were calculated after filtration of whole blood under the same condition as described in Example 1, and the results were 90%, 80% and 67%, respectively.

EXAMPLE 4

Chitosan having an average molecular weight of 450,000 and a deacetylation degree of 85% was dissolved in 1% acetic acid to obtain a solution of 3% chitosan. This solution was cast into the film and the cast film was dried under vacuum at 50° C. for 24 hours and then was made into pieces of about 10 mm×10 mm×0.5 mm in size. Leucocyte concentrate (Red Cross Blood Banks) was diluted 4 times using a physiological saline and the film was immersed into the solution.

The relative adsorption rate of leucocytes was expressed by the percent of the number of leucocytes before and after immersing the film into the leucocyte concentrate. After immersion of 10, 30, 60, 90 and 120 minutes, the relative adsorption rates of leucocytes were found to be 16%, 40%, 70%, 72% and 89%, respectively.

EXAMPLE 5

The procedures as described in Example 4 were repeated except that chitosan having an average molecular weight of 470,000 and a deacetylation degree of about 90% was used. The adsorption rates of leucocytes after immersion of 10, 30, 60, 90 and 120 minutes were found to be 22%, 41%, 79%, 82% and 93%, respectively.

EXAMPLE 6

The procedures as described in Example 4 were repeated except that chitosan having an average molecular weight of 420,000 and a deacetylation degree of about 95% was used. The adsorption rates of leucocytes after immersion of 10, 30, 60, 90 and 120 minutes were found to be 25%, 43%, 81%, 85% and 99%, respectively.

EXAMPLE 7

Chitosan having an average molecular weight of 550,000 and a deacetylation degree of 95% obtained from crab was dissolved in 1% acetic acid to obtain a solution of 1% chitosan and the procedures as described in Example 1 were repeated to prepare a filter. The removal rate of leucocytes and the recovery of platelets were calculated after the filtration of blood under the same condition as described in Example 1 and the results were 99% and 97%, respectively.

When a solution of 1% chitosan in 1% acetic acid, having an average molecular weight of about 700,000 and a deacetylation degree of about 90% was used under the same condition, the removal rate of leucocytes and the recovery of platelets were found to be 90% and 80%, respectively.

EXAMPLE 8

The procedures as described in Example 1 were repeated to prepare a filter except that the average molecular weight of chitosan and the concentration of coating solution in 1% acetic acid were varied as follows. The removal rate of leucocytes and the recovery of platelets were shown in Table 1.

TABLE 1

| Average Molecular Weight | Concentration | Removal rate of leucocytes | Recovery of platelets |
| --- | --- | --- | --- |
| 500,000 | 1% | 98% | 94% |
| 320,000 | 10% | 95% | 95% |
| 136,000 | 20% | 91% | 80% |

EXAMPLE 9

Chitosan having an average molecular weight of 500,000 and a deacetylation degree of 90% was dissolved in 1% acetic acid to obtain a coating solution of 2% chitosan. The same non-woven fabric as Example 1 was immersed into the coating solution and subjected to ultrasonic treatment with 40 kHz at room temperature for about 60 minutes. The removal rate of leucocytes and the recovery of platelets and red blood cells which were calculated after filtration of a whole blood under the same condition were found to be 99%, 95% and 95%, respectively.

EXAMPLE 10

Chitosan having an average molecular weight of 400,000 and a deacetylation degree of 90% was dissolved in 1% acetic acid to obtain a coating solution of 5% chitosan. The same non-woven fabric as Example 1 was immersed into the solution and subjected to ultrasonic treatment with 40 kHz at room temperature for about 90 minutes. The removal rate of leucocytes and the recovery of platelets and red blood cells which were calculated after filtration of a whole blood under the same condition were found to be 90%, 95% and 95%, respectively.

COMPARATIVE EXAMPLE 1

Non-coated, non-woven fabric was evaluated according to the same procedure as described in Example 1. The removal rate of leucocytes and the recovery of platelets and red blood cells were found to be 45%, 70% and 69%, respectively.

As shown in the above result, a filter comprising only non-woven fabric of polyester fiber has a low removal rate of leucocyte as well as a low transmittance efficiency for fibrin, protein gel, platelet, etc., and thus, is less effective for a filter for removal of leucocytes.

What is claimed is:

1. A process for removing leucocytes from blood comprising passing blood through a filter comprising non-woven fabric wherein the surface of the non-woven fabric is coated with a coating consisting essentially of chitosan having a deacetylation degree of 85 to 95% and an average molecular weight of 200,000 to 700,000, and wherein the non-woven fabric comprises natural or synthetic fiber having not more than 3 $\mu$m of pore size.

2. The process of claim 1, wherein the coating consists of said chitosan.

* * * * *